(12) United States Patent
Murphy (10) Patent No.: US 6,635,476 B1
(45) Date of Patent: Oct. 21, 2003

(54) TARGETED VECTORS

(75) Inventor: Richard B. Murphy, San Diego, CA (US)

(73) Assignee: Canji, Inc., San Diego, CA (US)

( * ) Notice: Subject to any disclaimer, the term of this patent is extended or adjusted under 35 U.S.C. 154(b) by 82 days.

(21) Appl. No.: 09/687,930

(22) Filed: Oct. 13, 2000

Related U.S. Application Data (60) Provisional application No. 60/159,782, filed on Oct. 15, 1999.

(51) Int. Cl.$^7$ .......................... C12N 15/00; C12N 15/09; C12N 15/63; C12N 15/70; C12N 15/74
(52) U.S. Cl. ................................. 435/320.1; 424/199.1; 424/93.1; 424/93.2; 435/235.1
(58) Field of Search ............................. 435/320.1, 455, 435/235.1; 424/9.1, 93.2, 199.1, 93.1

(56) References Cited

U.S. PATENT DOCUMENTS

| | | | |
|---|---|---|---|
| 4,569,794 A | 2/1986 | Smith et al. | 260/113 |
| 5,439,829 A | 8/1995 | Anderson et al. | 436/518 |
| 5,705,151 A | 1/1998 | Dow et al. | 424/93.21 |
| 5,723,287 A | 3/1998 | Russell et al. | 435/5 |
| 5,846,782 A | 12/1998 | Wickham et al. | 435/697 |
| 5,871,727 A | 2/1999 | Curiel | 424/93.2 |
| 5,882,877 A | 3/1999 | Gregory et al. | 435/320.1 |
| 5,885,808 A | 3/1999 | Spooner et al. | 435/172.3 |
| 5,932,210 A | 8/1999 | Gregory et al. | 424/93.2 |
| 5,965,541 A | 10/1999 | Wickham et al. | 514/44 |

OTHER PUBLICATIONS

Arnberg, et al., "Fiber Genes of Adenoviruses with Tropism for the Eye and the Genital Tract"; *Virology*, 227:239–244 (1997).

Douglas, et al., "Targeted gene delivery by tropism–modified adenoviral vectors"; *Nature Biotechnology*, vol. 14, 1574 (Nov. 1996).

Douglas, et al. "A system for the propagation of adenoviral vectors with genetically modified receptor specificities"; *Nature Biotechnology*, vol. 17, 470–475 (May 1999).

Harris, et al., "Strategies for targeted gene therapy"; *TIG*, vol. 12, No. 10 400–405 (Oct. 1996).

Michael, et al.; "Binding–incompetent Adenovirus Facilites Molecular Conjugate–mediated Gene Transfer by the Receptor–mediated Endocytosis Pathway"; *The Journal of Biological Chemistry*, vol. 268, No. 10 6866–6869 (Apr. 1993).

Michael, et al., "Addition of a short peptide ligand to the adenovirus fiber protein"; *Gene Therapy*, 2:660–668 (1995).

Nilson, et al., "Targeting of retroviral vectors through protease–substrate interactions"; *Gene Therapy*, 3:280–286 (1996).

Ohno, et al., "Cell–specific targeting of Sindbis virus vectors displaying IgG–binding domains of protein A"; *Nature Biotechnology*, vol. 15, 763–767 (Aug. 1997).

Stevenson, et al., "Selective Targeting of Human Cells by a Chimeric Adenovirus Vector Containing a Modified Fiber Protein"; *Journal of Virology*, vol. 71, No. 6 4782–4790 (Jun. 1997).

Watkins, et al., "The 'adenobody' approach to viral targeting: specific and enhanced adenoviral gene delivery"; *Gene Therapy*. 4:1004–1012 (1997).

Wickham, et al., "Increased In Vitro and In Vivo Gene Transfer by Adenovirus Vectors Containing Chimeric Fiber Proteins"; *Journal of Virology*, vol. 71, No. 11 8221–8229 (Nov. 1997).

Eck, et al., "Gene–based therapy"; Goodman & Gilman's The Pharmacological Basis of Therapeutics—Ninth Edition McGraw–Hill pp. 77–101 (1996).

Kabanov & Kabanov "DNA Complexes with Polycations for the Delivery of Genetic Material into Cells" *Bioconjugate Chem.*, vol. 6, pp. 7–20 (1995).

Verma, et al. "Gene Therapy—promises, problems and prospects"; *Nature*, vol. 389, pp. 239–242 (Sep. 1997).

*Primary Examiner*—Scott D. Priebe
*Assistant Examiner*—Brian Whiteman
(74) *Attorney, Agent, or Firm*—Townsend and Townsend and Crew LLP (57) ABSTRACT

This invention provides therapeutic and diagnostic agent delivery vehicles, including viral vectors, that are complexed to a targeting moiety by coordinate covalent linkages mediated by a transition metal ion. The complex is typically formed with a transition metal ion that is in a kinetically labile oxidation state; after the complex is formed, the oxidation state of the transition metal ion is changed to one that renders the complex kinetically stable. The use of a coordinate covalent linkage to attach the targeting moiety to the delivery vehicle provides the ability to readily attach a different targeting moiety to a delivery vehicle without modifying the delivery vehicle itself. This flexibility is achieved without sacrificing stability of the complex.

26 Claims, 2 Drawing Sheets

TARGETED VECTORS

CROSS-REFERENCE TO RELATED APPLICATION

This application claims benefit of U.S. Provisional Application No. 60/159,782, filed Oct. 15, 1999, which application is incorporated by reference for all purposes.

STATEMENT REGARDING FEDERALLY SPONSORED RESEARCH

Not Applicable.

BACKGROUND OF THE INVENTION

1. Field of the Invention

This invention pertains to the field of targeting of gene delivery systems (viral and non-viral) to particular cell and tissue types.

2. Background

The use of recombinant viral vectors for the delivery of exogenous genes to mammalian cells is well established. See e.g. Boulikas, T. in *Gene Therapy and Molecular Biology Volume* 1, pages 1–172 (Boulikas, Ed.) 1998, Gene Therapy Press, Palo Alto, Calif. However, certain viral vectors commonly used in such instances, such as adenoviruses, exhibit a broad tropism which permits infection and expression of the exogenous gene in a variety of cell types. While this can be useful in some instances, the treatment of certain diseases is enhanced if the virus is able to be modified so as "target" (i.e., to preferentially infect) only a limited type of cell or tissue.

A variety of approaches to create targeted viruses have been described in the literature. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham et al. (1997) *J. Virol.* 71(11):8221–8229 (incorporation of RGD peptides into adenoviral fiber proteins); Arnberg et al. (1997) *Virology* 227:239–244 (modification of adenoviral fiber genes to achieve tropism to the eye and genital tract); Harris and Lemoine (1996) *TIG* 12(10):400–405; Stevenson et al. (1997) *J. Virol.* 71(6):4782–4790; Michael et al. (1995) *Gene Therapy* 2:660–668 (incorporation of gastrin releasing peptide fragment into adenovirus fiber protein); and Ohno et al. (1997) *Nature Biotechnology* 15:763–767 (incorporation of Protein A-IgG binding domain into Sindbis virus).

However, the design of a functional chimeric protein for targeting is not facile. For example, if one wishes to create a chimeric adenoviral knob protein containing an targeting domain, the recombinant knob protein must be able to (a) assemble properly into the icosahedral viral structure and (b) also retain the binding specificity of the targeting moiety. This may involve significant and complex molecular modeling to incorporate the targeting moiety into the appropriate region of the knob protein to insure that the targeting moiety is on the surface of the knob protein. Additionally, since the precise process for assembly of the adenoviral particle is poorly understood it is possible that insertion of a large targeting moiety will sufficiently interrupt the three dimensional structure of the viral protein so that it does not efficiently assemble into an infectious virion. Furthermore, whenever one wishes to change the targeting properties of the adenovirus, it is necessary to reengineer the knob protein taking into account all of the foregoing, which can be a lengthy process. Moreover, the manipulation of the adenoviral genome to obtain a gene that encodes the chimeric protein is a time consuming process, due to the size and complexity of the adenoviral genome.

In order to avoid these hurdles, other methods of cell specific targeting rely on the conjugation of antibodies or antibody fragments to the envelope proteins (see, e.g. Michael et al. (1993) *J. Biol. Chem.* 268:6866–6869, Watkins et al. (1997) *Gene Therapy* 4:1004–1012; Douglas et al. (1996) *Nature Biotechnology* 14: 1574–1578. This approach also has its limitations. First, in the case of chemically conjugating the antibody (or antibody fragment) to the surface of the virion, the linkage is generally achieved by modification of amino acyl side chains in the antibody (particularly through lysine residues). As it is difficult to control the stoichiometry of this reaction, one can envision the resulting virion being coated with antibodies in a variety of orientations. As the binding specificity of the antibody is contained in the variable regions, the random association of the cross-linked antibody will result in many of the antibody variable domains being "hidden" and thus ineffective. Accordingly, in order to insure a sufficient number of exposed variable domains to achieve efficient targeting, a significant excess of antibody must be complexed to the virion. Additionally, the coating of the virion with an excess of antibodies may interfere with internalization of the virus in the target cell. For example, in the case of adenoviruses, the interaction between the viral coat proteins and the CAR receptor is believed to be an essential step in the infectious process. If the viral coat proteins are obscured by an excess of antibody proteins, one may expect that the efficiency of binding to the CAR receptor and internalization would suffer. If the virion is unable to infect the cell and exert its therapeutic effect, it is questionable whether this targeting approach would provide significant therapeutic benefit.

Alternative to the use of antibodies, others have complexed targeting proteins to the surface of the virion. See, e.g. Nilson et al. (1996) *Gene Therapy* 3:280–286 (conjugation of EGF to retroviral proteins). However, this approach suffers many of the same limitation as the use of antibodies, such as obscuring viral coat proteins and potentially interfering with the infectious mechanism.

In one attempt to avoid these problems, some groups have used anti-knob or anti-fiber antibodies complexed to a targeting moiety (see, e.g., U.S. Pat. No. 5,871,727). While this avoids the problem of having a antibody-coated virion as discussed above, such non-covalent complexes are in equilibrium with the free conjugated antibody and virion species, i.e.

$$\{\text{conjugated antibody-virion}\} \leftrightarrows \text{conjugated-antibody} + \text{virion}.$$

While the affinity of the antibody for the knob may be high and the resulting equilibrium constant of this reaction suggests the formation of a "stable" complex, this does not indicate that the complex will be kinetically stable in solution over a period of time. Additionally, although a complex may be "stable" in a solution of limited volume, upon introduction of the complex to a solution of essentially infinite volume (e.g., the bloodstream of a mammal) the equilibrium will be shifted in favor of dissociation of such a complex.

SUMMARY OF THE INVENTION

The present invention provides targeted complexes that are useful for delivering molecules to a particular cell or tissue type of interest. The invention provides targeted complexes of the formula:

{(delivery vehicle-CM)-TMI-(CM-targeting ligand)};

The delivery vehicle can be, for example, a peptide vector, a peptide-DNA aggregate, a liposome, a gas-filled microsome, an encapsulated macromolecule, and the like. In some embodiments, the delivery vehicle is a viral vector. Particularly suitable viral vectors include a retrovirus, a vaccinia virus, a herpes virus, an adeno-associated virus, a minute virus of mice (MVM), a human immunodeficiency virus, a sindbis virus, an MoMLV, and a hepatitis virus.

"CM" is a chelating moiety, such as a chelating peptide or an organic chelating agent. TMI is a transition metal ion. CM-targeting ligand is a chelating moiety (CM) covalently linked to a targeting ligand that can bind to a cell or tissue of interest.

The invention also provides methods for producing a kinetically inert targeted delivery vehicle complex. These methods involve: a) preparing a kinetically labile transition metal complex by contacting a delivery vehicle-CM and a CM-targeting ligand with a transition metal ion that is in a kinetically labile oxidation state; and b) changing the oxidation state of the metal ion to form the kinetically inert complex.

Also provided by the invention are methods of delivering a therapeutic or diagnostic agent to a target cell in an organism. These methods involve administering to an organism a targeted complex of the formula:

{(delivery vehicle-CM)-TMI-(CM-targeting ligand)};

wherein delivery vehicle-CM is a delivery vehicle that displays on its surface a polypeptide that comprises a chelating moiety (CM), TMI is a transition metal ion, and CM-targeting ligand is a chelating moiety (CM) covalently linked to a targeting ligand that binds to the target cell.

DETAILED DESCRIPTION

Figure 1:
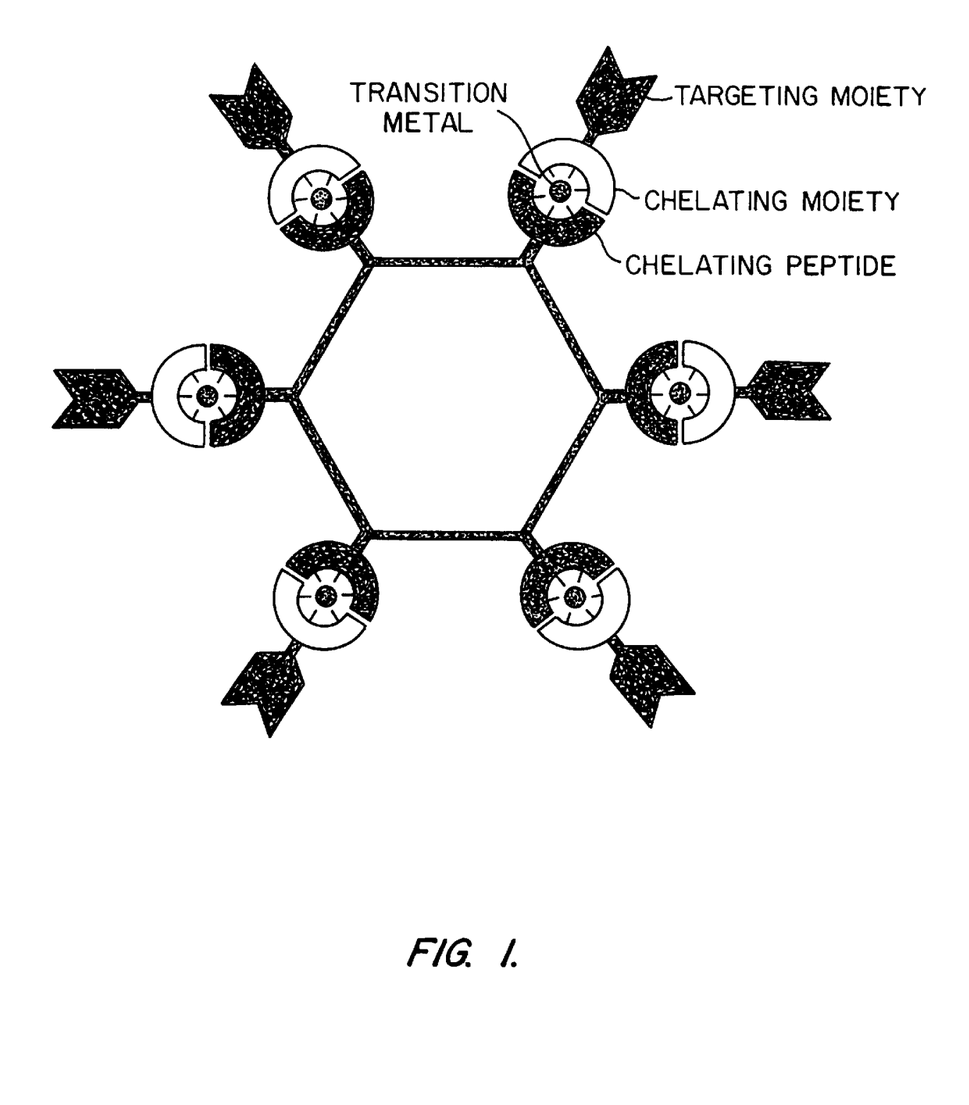
FIG. 1 is an illustration of one embodiments of the complexes of the present invention. The drawing provides is a diagrammatic representation of a complex wherein the virus is an adenovirus is containing a modified knob domain containing a chelating peptide and the targeting moiety is a single chain antibody containing a chelating peptide chelating moiety.
Figure 2:
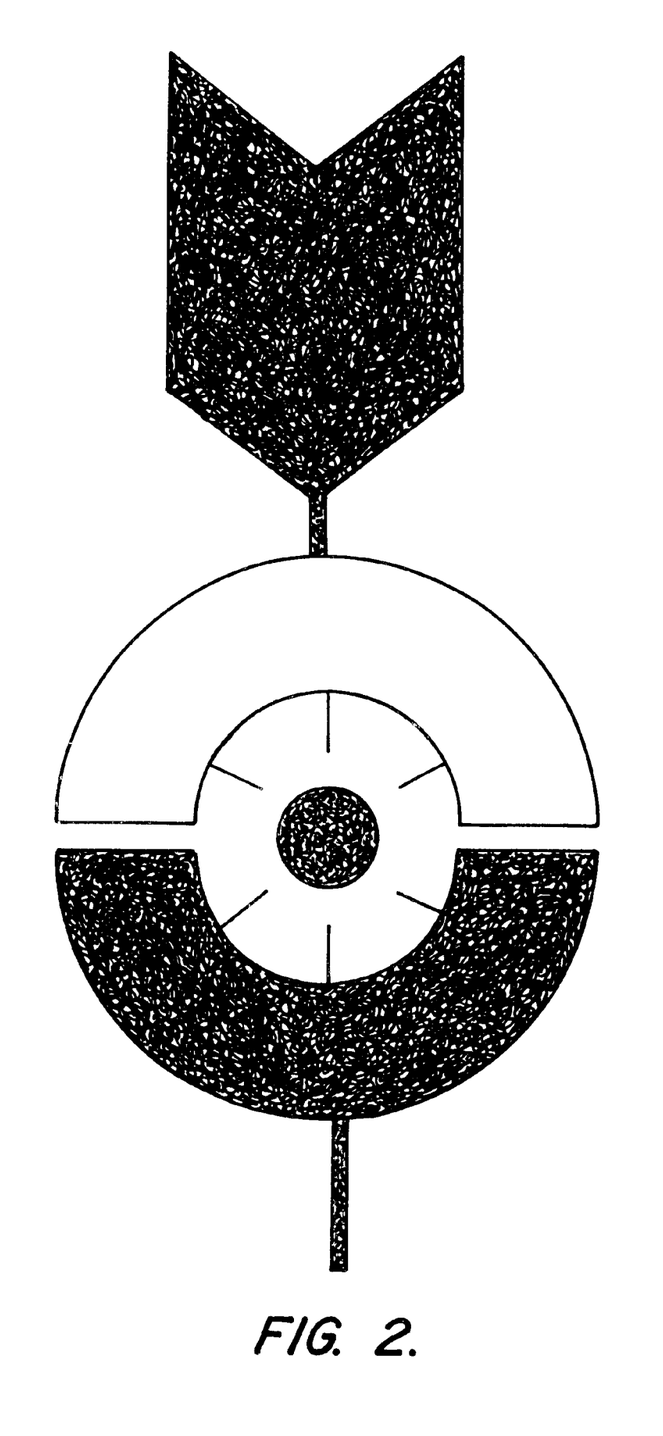
FIG. 2 is an enhanced diagrammatic representation of the linkage of the targeting moiety to the modified viral coat protein. The central circular entity represents a transition metal ion. The semi-circular structure shaded by cross-hatching represents the chelating moiety which is covalently linked to the targeting moiety. The semi-circular structure shaded with the dots represents the viral coat protein which has been modified to contain a chelating peptide.

The present invention provides viral vectors and other delivery vehicles to which targeting ligands are attached by a kinetically inert coordinate covalent linkage. The targeting ligands allow the delivery vehicle to be targeted to a particular cell or tissue type. The viral vectors, for example, display on their virion surface a coat protein that has been modified to include a chelating peptide. The targeting ligand is attached to a chelating moiety (e.g., a chelating peptide or an organic chelating agent), and a transition metal ion is employed to form a coordinate covalent bond with the modified coat protein and the targeting ligand. A coordinate covalent bond occurs when a given species donates a lone electron pair to a vacant orbital in another species.

The use of a coordinate covalent bond as a means to attach the targeting ligand to the gene delivery system provides significant advantages over previously available methods for targeting vectors, which have significant limitations as previously discussed. First, one need not reengineer a viral genome, for example, to modify the gene that encodes the surface protein each time one wishes to use a different targeting ligand. One simply employs a different CM-targeting ligand to retarget the vector and modify its tropism. Second, coordinate covalent complexes are kinetically inert, resulting in a long-lasting targeted vector. In contrast, attachment of targeting ligands by means of non-covalent linkage, for example, antibodies that bind to viral coat proteins is not kinetically inert.

It is essential that one appreciate the distinction between a kinetically inert and a thermodynamically stable complex. This distinction is discussed in detail in Anderson et al. (U.S. Pat. No. 5,439,829 issued Aug. 8, 1995). Thermodynamic stability refers to the thermodynamic tendency of a species to exist under equilibrium conditions. A kinetically inert complex, on the other hand, is one that is not labile, i.e., a particular complexed ion is not able to readily engage in reactions that result in replacement of one or more ligands in its coordination sphere by others. For example, in an aqueous environment, unoccupied coordination positions on a transition metal ion are occupied by water. A chelating peptide or other chelating agent must displace the water molecules to form a complex. When such reactions occur rapidly, the reaction is termed "labile." However, where such reactions occur very slowly or not at all, the complex is said to be kinetically "inert." Kinetic lability or inertness, unlike thermodynamic stability or instability, is thus related to the reaction rate. A complex can be thermodynamically stable even though the on/off reactions occur very rapidly (see, e.g., *Advanced Inorganic Chemistry*, Cotton, F. A. and Wilkinson, G. (1972) 3rd ed. Interscience Publishers, p.652). Conversely, a complex can be kinetically inert, and thus last for periods of time ranging from days to years, even though the complex is thermodynamically unstable (equilibrium lies in favor of dissociation) because the rate of dissociation is low.

While the affinity of an antibody for a particular protein may be high and the resulting equilibrium constant of this reaction suggests the formation of a "stable" complex, this does not indicate that the complex will be kinetically stable in solution over a period of time. This presents a particularly serious drawback when such non-covalent interactions are used to attach a targeting ligand to a delivery system which is then introduced into a biological system. The increased volume upon introduction of the complex to an organism will result in an equilibrium constant ($K_{eq}$) favoring dissociation, since the blood volume is essentially infinitely large in comparison to the administered volume. Furthermore, the toxicity of the free components of the complex may provide an additional degree of uncertainty in the use of such complexes in mammalian systems. Since non-covalently linked complexes will necessarily result in free species upon administration to an organism, the toxicity of the free species in addition to the complex would need to be evaluated. In human beings, this would likely complicate the regulatory approval process for such complexes as it would require additional toxicology clinical studies. These problems are avoided by the present invention, which uses a kinetically inert coordinate covalent linkage to attach the targeting ligand to the viral coat protein or other gene delivery system.

I. Targeted Complexes

Generally, the targeted complexes of the invention can be represented by the formula:

$$\{(\text{delivery vehicle-CM})\text{-TMI-}(\text{CM-targeting ligand})\} \quad (1)$$

wherein delivery vehicle-CM refers to a delivery vehicle that displays on its surface a chelating moiety, TMI is a transition metal ion, and CM-targeting ligand is a chelating moiety (CM) covalently linked to a targeting ligand. In presently preferred embodiments, the delivery vehicle is a viral vector, the chelating moiety is a chelating peptide, and the polypeptide to which the chelating peptide is attached is a viral coat protein.

A. Viral Vectors and Other Delivery Vehicles

The present invention provides complexes in which a viral vector or other delivery vehicle is attached by a coordinate covalent linkage to a targeting ligand. Such delivery vehicles include, in addition to viral vectors, other molecules or carriers that are useful for delivering an agent to a cell. Liposomes, for example can be engineered to accept the coordinate covalently linked targeting ligands, as can molecules that bind to nucleic acids or other agents.

In some embodiments, the complexes include a viral vector to which targeting ligands are attached. The term "virus" is used in its conventional sense to refer to any of the obligate intracellular parasites having no protein-synthesizing or energy-generating mechanism and generally refers to any of the enveloped or non-enveloped animal viruses commonly employed to deliver exogenous transgenes to mammalian cells. The viruses possess virally encoded viral coat proteins. The viruses useful in the practice of the present invention include recombinantly modified enveloped or non-enveloped DNA and RNA viruses. In presently preferred embodiments, the viruses are selected from baculoviridiae, parvoviridiae, picornoviridiae, herpesviridiae, poxviridae, or adenoviridiae. Chimeric viral vectors which exploit advantageous elements of each of the parent vector properties (See e.g., Feng et al. (1997) *Nature Biotechnology* 15:866–870) can also be employed in the practice of the present invention.

Viral vector systems useful in the practice of the instant invention include, for example, naturally occurring or recombinant viral vector systems. For example, viral vectors can be derived from the genome of human or bovine adenoviruses, vaccinia virus, herpes virus, adeno-associated virus (see, e.g., Xiao et al., *Brain Res.* 756:76–83 (1997), minute virus of mice (MVM), HIV, sindbis virus, and retroviruses (including but not limited to Rous sarcoma virus), and MoMLV, hepatitis B virus (see, e.g., Ji et al., *J. Viral Hepat.* 4:167–173 (1997). Typically, genes of interest are inserted into such vectors to allow packaging of the gene construct, typically with accompanying viral DNA, followed by infection of a sensitive host cell and expression of the gene of interest. One example of a preferred recombinant viral vector is the adenoviral vector delivery system which has a deletion of the protein IX gene (see, International Patent Application WO 95/11984, which is herein incorporated by reference in its entirety for all purposes).

In some instances it may be advantageous to use vectors derived from a different species from that which is to be treated in order to avoid the preexisting immune response. For example, equine herpes virus vectors for human gene therapy are described in WO98/27216 published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO 97/06826 published Apr. 10, 1997.

The virus can be replication competent (e.g., completely wild-type or essentially wild-type such as Ad d1309 or Ad d1520), conditionally replicating (designed to replicate under certain conditions) or replication deficient (substantially incapable of replication in the absence of a cell line capable of complementing the deleted functions). Alternatively, the viral genome can possess certain modifications to the viral genome to enhance certain desirable properties such as tissue selectivity. For example, deletions in the E1a region of adenovirus result in preferential replication and improved replication in tumor cells. The viral genome can also modified to include therapeutic transgenes (as more fully described below). The virus can possess certain modifications to make it "selectively replicating," i.e. that it replicates preferentially in certain cell types or phenotypic cell states, e.g., cancerous. For example, a tumor or tissue specific promoter element can be used to drive expression of early viral genes resulting in a virus which preferentially replicates only in certain cell types. Alternatively, one can employ a pathway-selective promoter active in a normal cell to drive expression of a repressor of viral replication. For example, a conditionally replicating adenoviral vector can be created by the use of a promoter active in the presence of endogenous p53 to drive expression of the E2F-Rb fusion protein (a potent inhibitor of the E2 adenoviral promoter). In such instances, where there is a defect in the p53 pathway such that active p53 is not present (e.g., a tumor cell), the repressor of viral replication is not expressed and the virus will replicate. However, where p53 is present (e.g. normal cells) the repressor of viral replication is expressed and viral replication is prevented. Selectively replicating adenoviral vectors that replicate preferentially in rapidly dividing cells are described in International Patent Application No. WO1999US0021451 (Publ. No. WO 0022136) entitled "Recombinant EIA Deleted Adenoviral Vectors." These vectors contain modifications to the E1a coding sequence so as to produce E1a gene products that are deficient in binding to one or more E1a p300 protein family members and one or more Rb protein family members, but retain the transactivating function of the E1a CR3 domain. Selectively replicating viruses are also described in International Patent Application No. WO1999US0021452 (Publ. No. WO 0022137), which is entitled "Selectively Replicating Viral Vectors." These viral vectors replicate in cells that have a defective pathway (e.g., a p53 or TGF-beta pathway), but not in cells with an active Additionally, the viral vector may be replication deficient or defective in that it possesses certain modifications to the viral genome so as to essentially deprive the virus of its ability to replicate in cells that are not capable to complementing the deleted adenoviral functions. For example, recombinant adenoviral vectors possessing a deletion of E1 gene functions are essentially unable to replicate except in cell lines that have been engineered to complement E1 functions, such as 293 cells, PERC.6 cells or A549-E1 cells. Such replication defective vectors have been used effectively to deliver therapeutic transgenes, such as the p53 tumor suppressor gene. Replication defective viral vectors are preferably derived from adenovirus serotypes 2 or 5 and possess deletions or mutations in the E1 region rendering one or more early genes inoperative so as to attenuate the replication of the virus in non-complementing cells. Additional deletions in the non-essential E3 region are also permissible to increase the packaging capacity of such vectors. Replication defective adenoviral vectors may also contain mutations or deletions so as to substantially eliminate protein IX function. Particularly preferred adenoviral vectors are described in Gregory et al., U.S. Pat. No. 5,932,210, issued Aug. 3, 1999. Alternatively, where large DNA inserts are desired to achieve the therapeutic effect in the target cell, a "gutted" or minimal viral vector system can be employed. Such vectors are well known in the art and a review of this technology is provided in Morsy and Caskey, *Molecular Medicine Today*, January 1999 pp. 18–24; Zhang, et al. (WO98/54345A1 published Dec. 3, 1998); and Kochanek et al. (1996) *Proc. Nat'l. Acad. Sci. USA* 93: 5731–5736.

In a presently preferred embodiment of the invention, the virus is an adenovirus. The use of adenoviral vectors for the delivery of exogenous transgenes are well known in the art. See, e.g., Zhang, W—W. (1999) *Cancer Gene Therapy* 6:113–138. The term "adenovirus" refers collectively to animal adenoviruses of the genus mastadenovirus including, but not limited to, human, bovine, ovine, equine, canine, porcine, murine and simian adenovirus subgenera. In particular, human adenoviruses include the A-F subgenera as well as the individual serotypes thereof the individual serotypes and A-F subgenera including but not limited to human adenovirus types 1, 2, 3, 4, 4a, 5, 6, 7, 8, 9, 10, 11 (Ad 11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The bovine adenoviruses useful in the invention include, but are not limited to, bovine adenovirus types 1,2,3,4,7, and 10. Canine adenoviruses, as used herein, includes but is not limited to canine types 1 (strains CLL, Glaxo, RI261, Utrect, Toronto 26-61) and 2. Equine adenoviruses of interest include, but are not limited to, equine types 1 and 2 and porcine adenoviruses of interest include, for example, porcine types 3 and 4. In a presently preferred practice of the invention, the virus is an adenovirus of serotype 2 or 5.

Adenoviral polypeptides into which one can incorporate a chelating peptide include, for example, the fiber protein (see, e.g., U.S. Pat. Nos. 5,846,789, 5,770,442, 5,543,328 and 5,756,086), the penton base protein (see, e.g., U.S. Pat. Nos. 5,559,099, 5,731,190 and 5,712,136), and the hexon protein (see, e.g., U.S. Pat. No. 5,922,315).

Retroviral vectors can also be targeted using the coordinate covalent complexes of the present invention. The envelope protein of retroviral vectors is modified to include a chelating peptide. The retroviral gene that encodes the env polypeptide is modified so that a fusion between a chelating peptide and all or part of the env polypeptide is expressed. Modifications of retroviral env-encoding genes are described in, for example, U.S. Pat. Nos. 5,869,331. U.S. Pat. No. 5,736,387 describes the use of chimeric targeting proteins that include a ligand (e.g., a cytokine analog) that is capable of binding to a cytokine receptor to target retroviral vectors to cells that display the cognate cytokine receptor. Viral vectors having a chimeric envelope protein that binds to cell surface receptors are described in, for example, U.S. Pat. No. 5,985,655. The present invention allows such targeting schemes to be accomplished without having to modify the viral genome for each different targeting moiety.

Other suitable viral vectors include paramyxovirus, such as simian virus 5 (SV5), a common and non-pathogenic RNA virus. Two viral glycoproteins are found in the envelope of SV5: the HN protein which functions in attachment to host cell receptors, and the F protein which fuses the virion envelope with the target cell plasma membrane. U.S. Pat. No. 5,962,275 describes the engineering of SV5 to encode a foreign protein in place of the normal viral attachment protein HN. Virions containing the foreign membrane protein in the viral envelope are specific to cells expressing the ligand that is complementary to the virion-associated foreign protein or glycoprotein. The present invention provides a means to make such chimeric envelope proteins without having to alter the viral genome each time a different targeting moiety is used. Instead, the viral genome is modified to express at least the virion-bound portion of the HN protein fused to a chelating moiety. No additional changes to the viral genome are then required to substitute one targeting moiety for another. One simply expresses the desired targeting moiety, linked to a chelating moiety, and attaches it to the generic virion.

Bacteriophage are another delivery system to which the present invention is applicable. Targeted bacteriophage vectors are described in, for example, U.S. Pat. No. 6,054,312.

In some presently preferred embodiments, the viral vector is modified so as to reduce or eliminate the native tropicity of the virus. For example, the interaction of the a native viral envelope protein with a cell surface receptor is often highly specific and determines cell-type specificity of a particular virus (Weiss et al. (1985) *RNA tumor viruses*, Cold Spring Harbor Laboratory, Cold Spring Harbor, N.Y.). Therefore, by engineering the chelating peptide so that the portion of the env polypeptide that confers cell specificity is disrupted or eliminated, one can obtain a targeted viral complex that is not only has enhanced affinity for the cell or tissue type that is recognized by the targeting ligand, but also has reduced or eliminated affinity for the natural target cell. Similarly, infection of adenoviruses into susceptible cells involves the binding of the adenovirus fiber protein (in particular, the C-terminal knob domain) to the coxsackievirus and adenovirus receptor (CAR), which serves as the primary cellular receptor. The subsequent internalization of the virion involves Arg-Gly-Asp (RGD) sequences in the penton base, which interact with the secondary host cell receptors, integrins $\alpha_v\beta3$ and $\alpha_v\beta5$. Thus, by disrupting either or both of the fiber protein and the penton base, one can eliminate the native tropicity of the adenoviral vector (see, e.g., Douglas et al. (1999) *Nature Biotechnology* 17: 470–475; U.S. Pat. No. 5,885,808). The disruption of proteins involved in native viral tropism can be as an intended consequence of the introduction of the chelating peptide, or can be accomplished by other manipulations of the viral genome. Parvoviral vectors are another example of viral vectors that can be targeted using the modified coat protein-chelating peptide complexed to a targeting ligand.

The invention also provides complexes in which a conformationally restrained non-native amino acid sequence is attached to a surface-displayed chelating moiety. Conformationally constrained peptides are generally more effective in targeting delivery to specific cells and/or tissues than unconstrained peptides. U.S. Pat. No. 6,057,155 describes the use of such conformationally-restrained, or "constrained" amino acid sequences in a chimeric adenovirus fiber protein. The ability of the chimeric fiber protein to bind to the cell and/or mediate cell entry is increased, e.g., relative to the wild-type protein. According to U.S. Pat. No. 6,057,155, the conformational constraint can be achieved by placing a nonnative amino acid sequence in an exposed loop of the chimeric fiber protein, or, through the placement of the sequence in another location and creation of a loop-like structure comprising the nonnative amino acid sequence at that site. The present invention facilitates making the chimeric fiber protein by eliminating the need to alter the viral genome in order to introduce the nonnative amino acid sequence. Rather, a polypeptide that includes a chelating moiety and the nonnative amino acid sequence and associated loop structure is made by, for example, recombinant expression. This polypeptide is then attached to a viral vector that displays a corresponding chelating moiety through a transition metal ion.

The invention also provides methods for reducing or eliminating the ability of a viral vector to be recognized by an antibody that could otherwise neutralize the vector. Neutralizing antibodies can, for example, inhibit entry of a vector into a cell, or inhibit vector-mediated gene expression. Therefore, by modifying coat proteins of the viral vector, one can reduce the susceptibility of the vector to neutralization. U.S. Pat. No. 6,127,525 describes modifying a viral coat protein to decrease or eliminate the ability of a neutralizing antibody to interact with an adenoviral vector. These coat protein modifications can include, for example, introducing non-native amino acids into the coat protein. For example, a portion of the coat protein amino acid sequence can be removed and replaced with a "spacer" amino acid sequence, or simply by introducing a "spacer" sequence to an unmodified naturally occurring coat protein. For example, the deletion of one or more hypervariable regions (e.g., the I1 loop and/or I2 loops) of the adenoviral hexon protein can result in reduced sensitivity to neutralizing antibodies. Prior to the instant invention, such modifications required altering the gene that encodes the respective coat protein (e.g., for adenovirus: penton base, hexon, or fiber protein). Through use of the invention, however, one can simply attach an appropriately modified extracellular region of the coat protein to a chelating moiety that is displayed on the surface of the virion using a transition metal ion. Thus, one can readily construct viral vectors that are appropriate for avoidance of different neutralizing antibodies without having to modify the viral genome. A chelating moiety-modified extracellular domain molecule is constructed (e.g., by recombinant expression) for the particular application and attached to the generic viral vector that displays a cell-surface chelating moiety.

Attachment of a targeting moiety by means of a coordinate covalent linkage according to the invention is useful not only for viral vectors, but also for other delivery vehicles. For example, one can attach a targeting ligand to a liposome using a coordinate covalent linkage. The liposomes used in these embodiments of the invention carry a chelating moiety on their surface. The chelating moiety can be, for example, a chelating peptide that is present on a polypeptide that is displayed on the surface of the liposome membrane. Alternatively chelating peptides or other chelating moieties can be attached chemically to lipids that comprise the liposome membrane. The use of coordinate covalent linkages for attaching a targeting ligand to a liposome is advantageous because only one liposome structure need be developed; once such structures having chelating moieties are made, it is a simple matter to attach a desired targeting ligand. It is not necessary to reengineer a liposome-anchored polypeptide or other anchoring moiety for each of the targeting moieties that are of interest.

Coordinate covalent linkages are also useful for attaching targeting moieties to other vehicles for delivering nucleic acids or other compounds. For example, one can use these linkages to attach a targeting moiety to a polycation, which is in turn complexed with a nucleic acid that is to be targeted to a particular cell or tissue (see, e.g., U.S. Pat. Nos. 5,874,297, 5,166,320, and 5,635,383). For example, gene constructs or other agents can be conjugated to a cell receptor ligand for facilitated uptake (e.g., invagination of coated pits and internalization of the endosome; see, e.g., Wu et al. (1988) J. Biol. Chem. 263:14621–14624; WO 92/06180; U.S. Pat. No. 5,871,727) through a coordinate covalent linkage. Again, the use of coordinate covalent attachment simplifies the attachment of the targeting ligand molecules to the delivery vehicle.

Other suitable delivery systems include, but are not limited to, an HVJ (Sendai virus)-liposome gene delivery system (see, e.g., Kaneda et al., Ann. N.Y. Acad. Sci. 811:299–308 (1997)); a "peptide vector" (see, e.g., Vidal et al., CR Acad. Sci III 32:279–287 (1997)); a peptide-DNA aggregate (see, e.g., Niidome et al., J. Biol. Chem. 272:15307–15312 (1997)); lipidic vector systems (see, e.g., Lee et al., Crit Rev Ther Drug Carrier Syst. 14:173–206 (1997)); polymer coated liposomes (Marin et al., U.S. Pat. No. 5,213,804, issued May 25, 1993; Woodle et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994); gas filled microspheres (Unger et al., U.S. Pat. No. 5,542,935, issued Aug. 6, 1996), encapsulated macromolecules (Low et al. U.S. Pat. No. 5,108,921, issued Apr. 28, 1992; Curiel et al., U.S. Pat. No. 5,521,291, issued May 28, 1996; Groman et al., U.S. Pat. No. 5,554,386, issued Sep. 10, 1996; Wu et al., U.S. Pat. No. 5,166,320, issued Nov. 24, 1992). In each case, the transition metal ion-mediated chelation methods of the invention can be used to attach a targeting moiety to the delivery vector.

In order to mask the immunogenic effects of the delivery system, especially viral vectors, it may be desirable to additionally complex agents such as polyethylene glycol (PEG) to the surface of the delivery system to minimize immunological clearance of the complex. Preferred PEGylation protocols are described in Frances et al. (1998) Int. J. Hematology 68:1–18 and commercialized by PolyMASC Pharmaceuticals PLC (London UK) as the "lipoMASC" and "viraMASC" technologies (www.polymasc.com).

B. Chelating Moiety (CM);

The delivery vehicles used in the targeted complexes of the present invention include a polypeptide or other molecule that is displayed on the surface of the delivery vehicle molecule, to which a chelating moiety is attached. The term "chelating moiety" (abbreviated herein as CM) refers collectively to chelating peptides and organic chelating agents. For example, a viral vector can have a coat protein that has been modified to include a chelating peptide. Another chelating moiety is attached to the targeting ligand. The targeting ligand is attached to the delivery vehicle by means of a transition metal ion that forms a coordinate covalent bond between the CM attached to the surface-displayed molecule on the delivery vehicle and the CM attached to the targeting ligand. The CM attached to the delivery vehicle can be the same as, or different than, the CM that is attached to the targeting ligand.

1. Chelating Peptide (CP)

The term "chelating peptide" (abbreviated "CP") refers to a peptide sequence that is capable of chelating a transition metal ion as described in Smith et al. (U.S. Pat. No. 4,569,794 issued Feb. 11, 1986) and Anderson et al. (U.S. Pat. No. 5,439,829 issued Aug. 8, 1995) the entire teachings of which are herein incorporated by reference. Generally, the chelating peptide is incorporated into the viral coat protein or other delivery vehicle polypeptide by modifying the viral coat protein coding sequence. The chelating peptide is incorporated into the delivery vehicle component at a location that will ensure its exposure on the delivery vehicle surface. The chelating peptide can be appended to the amino or carboxy terminus of the protein or can be incorporated internally into the delivery vehicle protein in an surface-exposed domain of the protein.

Examples of an adenovirus in which the knob protein has been modified to contain a metal chelating peptide are known in the art. For example, Douglas et al. describe a recombinant adenovirus in which a poly-His metal chelating peptide has been incorporated into the carboxy terminal domain of the adenoviral fiber protein (*Nature Biotechnology* (1999) 17: 470–475). The penton and hexon polypeptides are also suitable adenovirus coat proteins for introduction of the chelating peptide. Apart from the insertion of the metal chelating peptide in the coat protein, the remainder of the viral genome can be wild-type or can be modified through conventional recombinant DNA techniques to possess specific properties.

Chelating peptides that are useful in the targeted vectors of the invention include, for example, a polyhistidine sequence. Generally, at least two histidine residues are required to obtain binding to a transition metal ion; the use of additional adjacent histidines increases the binding affinity. Typically, six adjacent histidines are used, although one can use more or less than six. Suitable polyhistidine peptides are described in, for example, Anderson et al. (U.S. Pat. No. 5,439,829, issued Aug. 8, 1995), Doebli et al. (U.S. Pat. No. 5,284,993, issued Feb. 8, 1994) and Doebli et al. (U.S. Pat. No. 5,310,663, issued May 10, 1994).

In presently preferred embodiments, a nucleotide sequence that encodes a chelating peptide is incorporated into a gene that encodes a polypeptide that is displayed on the surface of a delivery vehicle, and/or the peptidyl targeting ligand. This typically involves constructing a fusion gene in which a nucleic acid that codes for the polypeptide is linked, in reading frame, to a nucleic acid that codes for the chelating peptide. In regard to coat proteins of a virus, the nucleic acid encoding the chelating peptide is preferably placed at a location in the surface polypeptide gene that does not disrupt the ability of the fusion protein obtained to be displayed on the surface of the delivery vehicle. Where the targeting ligand is an antibody, the chelating peptide-encoding nucleic acid can be placed at or near the region of the antibody gene that encodes the carboxyl terminus of either the light chain or the heavy chain, or both.

Similarly, when the CP-targeting ligand is created by recombinant means, the nucleotide sequence encoding the chelating peptide is incorporated into (or added to) the nucleotide sequence encoding the targeting ligand. The chelating peptide should not interfere with the ability of the targeting ligand to bind to the target cell or tissue type.

Methods for constructing and expressing genes that encode fusion proteins are well known to those of skill in the art. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning: A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Alternatively, one can generate CP-targeting ligand species by conventional chemical protein synthesis reactions. For example, an isolated protein can be modified to incorporate a chelating peptide by chemical linkage through the amino or carboxy termini, through free sulfhydryl groups or free E-amino groups of Lysine or Arg.

2. Organic Chelating Agent

The term "organic chelating agents" is used herein to refer non-peptidyl bidentate, tridentate, quadridentate, tripod, and macrocyclic ligands capable of chelating a transition metal ion. Examples of such organic chelators include iminodiacetic acid, nitrilotriacetic acid, terpyridine, bipyridine, triethylenetetraamine, biethylene triamine and derivatives thereof. Suitable chelating moieties are described in, for example, U.S. Pat. No. 5,439,829.

C. Transition Metal Ion (TMI)

The term "transition metal ion" (abbreviated as TMI), as described in Anderson et al., refers to a variety of metal ions capable of forming coordinate complex between at least two chelating moieties and possessing kinetically labile and kinetically inert oxidation states. Octahedral complexes with filled ($d^6$) or half-filled($d^3$) levels such as Cr(III), V(II), Mn(IV) and the low spin forms of Co(III), Fe(II), Ru(II), Os(II), Rh(III), Ir(III), Pd(IV), and Pt(IV) tend to be extremely inert and useful in the practice of the instant invention. Hanzik, Robert P. in *Inorganic Aspects of Biological and Organic Chemistry*, Academic Press, New York, 1976, p. 109. See also, Cotton, F. A. and Wilkinson, G. supra. In the preferred practice of the invention the metal ion is selected from the group comprising Te, Co, Cr, and Ru. In the most preferred practice of the invention the metal ion is Co. In the most preferred practice of the invention it is desirable to proceed from Co(II), Cr(II), or Ru(III) to Co(III), Cr(III), or Ru(II) respectively to form the inert complex. Producing the necessary change in the oxidation state of the metal ion can be achieved by a variety of redox reagents. For example, oxidizing agents such as oxygen, hydrogen peroxide, and peracids can be used in the practice of the invention. Examples of reducing agents include, for example, thiols, potassium ferrocyanide, potassium thiocyanate, sulfites, and sodium dithionite. These will be prepared in aqueous solutions of appropriate concentrations.

In some instances, one may wish to incorporate a metal ion which is readily detected by diagnostic testing equipment such as x-ray or magnetic resonance imaging. In this manner, a clinician can non-invasively follow the trafficking of the complex within an organism. Additionally, certain heavy metals such as $Te^{99}$ provide therapeutic (i.e., anti-tumor) effects and can be used to complement the efficacy of the vector.

D. Targeting Ligand

The term "targeting ligand" refers to molecules that interact with and bind to cell type surface ligands of particular cells. Examples of such targeting moieties include antibodies against cell surface proteins and ligands for cell surface proteins. Examples of cell surface proteins include tumor antigens, hormone receptors, G-protein coupled receptors, cytokine receptors, and the like.

1. Antibody

In some embodiments, the targeting ligand includes all or part of an antibody that binds to the desired target tissue or cell. The term "antibody" a term used to collectively describe antibodies, fragments of antibodies (such as, but not limited to, Fab, Fab', $Fab_2$' and Fv fragments), chimeric, humanized, or CDR-grafted antibodies capable of binding antigens of a similar chain polypeptide binding molecules" as described in PCT Application No. PCT/US 87/02208, International Publication No. WO 88/01649, International Publication Date: Mar. 10, 1988. Antibodies can be monoclonal or polyclonal, but are preferably monoclonal. The antibody can be derived from non-human sources (e.g., mice, rabbits, goats) but when the complexes are being used in the treatment of human beings, the antibody is preferably a "human" antibody derived from non-human sources. Transgenic mice have been developed which contain the entire human immunoglobulin gene cluster and as such are capable of producing "human" antibodies. Such technology and services are available from Abgenix, Inc., 7601 Dumbarton Circle, Fremont, Calif. 94555. As such antibodies are derived from human genes, such antibodies are preferred as targeting ligands due to a reduced potential immunogenicity to a human host. Again, fragments of such human antibodies are particularly preferred as targeting ligands. Single chain antibodies modeled on such human antibodies are particularly preferred as they can be prepared more economically in prokaryotic culture procedures.

2. Tumor Antigens

When the viral complex is being used to selectively target tumor cells, it is preferred that the targeting ligand is reactive with a tumor antigen. The term "tumor antigen" is used herein to refer to proteins present only on tumor cells (tumor specific antigens) as well as those present on normal cells but expressed preferentially on tumor cells (tumor associated antigens). The term tumor antigen includes, but is not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. Antibodies which react with such tumor antigens are commercially available or can be prepared through conventional techniques used for the generation of antibodies.

3. Ligands for Cell Surface Receptors/Proteins

Nearly every cell type in a tissue in a mammalian organism possesses some unique cell surface receptor, e.g., G-protein coupled receptors. Consequently, when targeting delivery of the complex to a particular cell type, it is possible to incorporate nearly any ligand for the cell surface receptor as a targeting ligand into the complex. For example, peptidyl hormones can be used a targeting moieties to target delivery to those cells which possess receptors for such hormones. Chemokines and cytokines can similarly be employed as targeting ligands to target delivery of the complex to their target cells. A variety of technologies have been developed to identify genes that are preferentially expressed in certain cells or cell states and one of skill in the art can employ such technology to identify ligands which are preferentially or uniquely expressed on the target tissue of interest. When the ligand is a non-peptidyl or non-protein ligand, it is preferred to employ an organic chelating agent covalently linked to the ligand. When the ligand is a protein or peptide, it is preferred that the chelating agent is a chelating peptide. Again, the chelating peptide can be incorporated at any convenient non-essential domain of the ligand. The preparation of recombinant proteins comprising chelating peptides is well known in the art and commercial vectors are available to facilitate the recombinant production of proteins incorporating chelating peptides such as the pBlueBacHis2 vector commercially available from Invitrogen, San Diego, Calif.

4. Other Ligands

Other suitable ligands include "totally synthetic affinity reagents," which are described in U.S. Pat. Nos. 5,948,635, 5,852,167 and 5,844,076. Binding polypeptides obtained by directed evolution, for example, as described in U.S. Pat. No. 5,837,500 can also be used.

Nuclear localization sequences (NLS) can also be attached to a vector using transition metal ion chelating methods of the invention. NLS facilitate trafficking of proteins into a cell nucleus. See, e.g., WO 96/41606 and U.S. Pat. No. 6,054,312.

II. Preparing the Targeted Complexes

The invention also provides methods of preparing kinetically inert transition metal complexes between a chelating peptide that is displayed on a delivery vehicle and a targeting ligand that is attached to a chelating moiety. The methods involve:

a) preparing a kinetically labile transition metal complex with a transition metal ion, the delivery vehicle-CM and the CM-targeting ligand, and b) changing the oxidation state of the metal ion to form the kinetically inert complex.

The formation of the complex while the metal ion is in its kinetically labile state and then converting the oxidation state to form a kinetically inert complex is advantageous the rate of complex formation with the transition metal ion in its inert state would be very low. If it is desired to dissociate the targeting ligand from the delivery vehicle, this can be accomplished simply by contacting the complex with an appropriate redox reagent to change the oxidation state back to the kinetically labile state.

For embodiments in which the delivery vehicle is a viral vector, the methods of the invention can involve preparing a recombinant viral protein wherein the viral coat protein possesses a chelating peptide. A recombinant targeting ligand that is attached to a chelating moiety is also prepared. The viral coat protein and the targeting ligand are then reacted with a transition metal ion that is in a kinetically labile oxidation state. To make the complex stable, the oxidation state of the transition metal ion is changed to a kinetically inert oxidation state. The kinetically inert complexes are then purified.

Each of the species to be complexed (i.e., the CM-delivery vehicle and the CM-targeting ligand) can be prepared as described above and isolated using conventional chromatographic techniques. Preferably, the CM-targeting ligand is purified to homogeneity using CP-IMAC purification as described in Smith et al. (U.S. Pat. No. 4,569,794) and the CM-virus purified in accordance with the teaching of Shabram et al. (U.S. Pat. No. 5,837,520 issued Nov. 17, 1998, the entire teaching of which is herein incorporated by reference). Alternatively the viral complex can be purified using conventional CsCl procedures.

The formation of a kinetically labile viral complex can be accomplished by adding the metal ion to the CM-delivery vehicle or the CM-targeting ligand independently, or both species can be exposed to the metal ion in a single reaction vessel. However, in order to maximize the yield and avoid the formation of homogenous polymers of delivery vehicle or dimers of targeting ligand-CM species, it is preferred that the metal ion be exposed to the targeting ligand, excess metal removed, and the targeting ligand containing the kinetically labile metal be exposed to the delivery vehicle containing the modified viral coat protein. Adding the metal to, for example, a viral vector first will likely result in polymerization of the viral particles and precipitation.

The formation of the kinetically inert complex can be achieved using a variety of oxidizing or reducing agents as described above and will depend on the nature of the metal ion involved. Care should be taken to use any particularly harsh conditions which would result in denaturing of the targeting ligand or CM-delivery vehicles.

The purification of the complexes can be accomplished using conventional chromatographic techniques. Preferably, the purification/isolation of the kinetically inert complexes should be performed in the presence of imidazole or a similar agent capable of competing with the formation of a kinetically labile intermediate. This will facilitate the purification of only kinetically inert complexes by disrupting kinetically labile complexes, thus insuring a homogenous kinetically inert complex.

III. Uses of the Targeted Complexes

The complexes of the present invention find use in a wide variety of applications. Among these applications are the targeting of therapeutic or diagnostic agents to particular cells or tissues.

A. Therapeutic Applications

The complexes of the present invention are useful in the treatment of a wide range of diseases in mammalian organisms. The term "mammalian organism" includes, but is not limited to, humans, pigs, horses, cattle, dogs, cats, and the like. In these embodiments, a therapeutic agent is carried in, or attached to, a viral vector, liposome, or other delivery vehicle, to which is complexed the targeting ligand through a transition metal ion.

The methods and compositions of the present invention can be used for the treatment of a variety of maladies common in mammalian organisms. For example, the formulations and methods of the present invention can be used for the treatment of a variety of mammalian species suffering from such maladies including humans, pigs, horses, cattle, dogs, cats. In a presently preferred practice of the invention, the mammalian species is a human being.

For example, these complexes are useful in the treatment of cancer wherein a viral or other vector targeted to a cancer cell is designed to kill the infected cell, and can be designed to have a by-stander effect so as to kill surrounding cancer cells. In such instances the targeting ligand of the complex can be an antibody against a tumor antigen or a ligand for a receptor preferentially expressed on target tumor cells. A wide variety of tumor antigens are well known in the art and antibodies to such antigens are available from commercial sources such as BioDesign International (105 York Street, Kennebunk, Me. 04043 USA). Generation of antibody fragments of such intact antibodies are well known to those of skill in the art. Additionally, such antibodies can be reengineered to be chimeric, humanized, etc.

In a particularly preferred embodiment of the invention, the targeting ligand is a single chain antibody directed against a tumor antigen such as CEA. Such single chain antibodies against tumor antigens are known in the art. For example, Anderson, et al., supra., describe the anti-CEA CHEL-13 single chain antibody containing a chelating peptide chelating moiety.

1. Gene Delivery

In some embodiments, the complexes of the present invention are used to deliver nucleic acids, including, for example, antisense nucleic acids, genes that encode therapeutic polypeptides, and the like, to specific cells and/or tissues. Nucleic acid delivery is useful for several applications, including corrective gene replacement therapy for defective genes, nucleic acid-mediated immunization, delivery of genes that encode therapeutic polypeptides, and cancer therapy.

a. Expression Systems.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked but not directly flanked and may even function in trans from a different allele or chromosome.

Expression of a nucleic acid, such as the production of a polypeptide or an antisense nucleic acid, is desired for many applications. Expression is typically accomplished by placing the nucleic acid to be expressed in an "expression cassette," which is a nucleic acid construct, generated recombinantly or synthetically, that includes nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

In order to effect expression of a nucleic acid of interest, the nucleic acid is operably linked to a promoter sequence operable in the mammal cell. Examples of promoters include, for example, viral promoters endogenous to genome of a viral vector, or promoters derived from other sources. The term "promoter" is used in its conventional sense to refer to a nucleotide sequence at which the initiation and rate of transcription of a coding sequence is controlled. The promoter contains the site at which RNA polymerase binds and also contains sites for the binding of regulatory factors (such as repressors or transcription factors). Promoters can be naturally occurring or synthetic. The promoters can be endogenous to the virus or derived from other sources. The promoter can be constitutively active, or temporally controlled (temporal promoters), activated in response to external stimuli (inducible), active in particular cell type or cell state (selective) constitutive promoters, temporal viral promoters or regulable promoters.

While the complexes of the present invention facilitate targeting to particular cells, under certain circumstances (particularly where the virus is designed to destroy the infected cell) it may be desirable to further regulate the replication of a replication competent virus or regulate the expression of the nucleic acid. In the preferred practice of the invention, the promoter is a selective promoter, i.e. promoters that are preferentially active in selected cell types or cell states. Examples of such selective promoters include tissue specific or tumor specific promoters. Tissue specific and tumor specific promoters are well known in the art and include promoters active preferentially in smooth muscle (alpha-actin promoter), epidermal specific (Polakowska et al. U.S. Pat. No. 5,643,746 issued Jul. 1, 1997) pancreas specific (Palmiter et al. (1987) *Cell* 50:435), liver specific (Rovet et al. (1992) *J. Biol. Chem.* 267:20765; Lemaigne et al. (1993) *J. Biol. Chem.* 268:19896; Nitsch et al. (1993) *Mol. Cell. Biol.* 13:4494), stomach specific (Kovarik et al. (1993) *J. Biol. Chem.* 268:9917), pituitary specific (Rhodes et al. (1993) *Genes Dev.* 7:913), prostate specific (Henderson, U.S. Pat. No. 5,648,478, issued Jul. 15, 1997), etc. The term "selective promoters" also includes promoters which have both tissue and tumor cell specificity for example the alpha-fetoprotein promoter is both liver specific and tumor specific replicating much more efficiently in hepatocellular carcinoma cells than in either non-tumor or non-liver cells.

The term "temporal promoters" refers to promoters which drive transcription or the therapeutic transgene at a point later in the viral cycle relative to the promoter controlling expression of the pathway-responsive promoter. Examples of such temporally regulated promoters include the adenovirus major late promoter (MLP), other promoters such as E3. In the preferred practice of the invention, the MLP promoter is employed. In the case of herpes simplex virus genomes, the Latent Activated Promoters is an example of such a temporally regulated promoter.

The term "inducible promoter" refers to promoters which facilitate transcription of the therapeutic transgene preferable (or solely) under certain conditions and/or in response to external chemical or other stimuli. Examples of inducible promoters are known in the scientific literature (see, e.g. Yoshida and Hamada (1997) *Biochem. Biophys. Res. Comm.* 230:426–430; Iida et al. (1996) *J. Virol.* 70(9):6054–6059; Hwang et al. (1997) *J. Virol.* 71(9):7128–7131; Lee et al. (1997) *Mol. Cell. Biol.* 17(9):5097–5105; and Dreher et al. (1997) *J. Biol. Chem.* 272(46); 29364–29371. Examples of radiation inducible promoters are described in Manome et al. (1998) *Human Gene Therapy* 9:1409–1417).

b. Therapeutic Transgenes

The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

1) Tumor Suppressor Genes

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4/Smad4 gene, the BRCA-1 gene, the BRCA-2 gene, the WT-1 gene, the retinoblastoma gene (Lee et al. (1987) *Nature* 329:642), the MMAC-1 gene, the adenomatous polyposis coli protein (Albertsen et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3 (Cheng et al. (1998) *Proc. Nat'l. Acad. Sci. USA* 95:3042–3047), the MTS1 gene, the CDK4 gene, the NF-1 gene, the NF2 gene, and the VHL gene.

2) Antigenic Genes

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilitate immune recognition, the antigenic gene may be fused to the MHC class I antigen.

3) Cytotoxic Genes

The term "cytotoxic gene" refers to nucleotide sequence, the expression of which in a cell produces a toxic effect. Examples of such cytotoxic genes include nucleotide sequences encoding Pseudomonas exotoxin, ricin toxin, diphtheria toxin, and the like. Cytotoxic genes are generally employed in the situation where the virus is designed to destroy the targeted cell and as such are particularly preferred in the treatment of cancer. Given the nature of the toxins produced by such genes, it is desirable to control the expression of such genes. Consequently, when the virus is designed to encode and express a cytotoxic gene, it is preferred that the promoter be highly selective or able to be closely regulated.

4) Cytostatic Genes

The term "cytostatic gene" refers to nucleotide sequence, the expression of which in a cell produces an arrest in the cell cycle. Examples of such cytostatic genes include p21, the retinoblastoma gene, the E2F-Rb fusion protein gene, genes encoding cyclin dependent kinase inhibitors such as p16, p15, p18 and p19, the growth arrest specific homeobox (GAX) gene as described in Branellec et al. (PCT Publication WO97/16459 published May 9, 1997 and PCT Publication WO96/30385 published Oct. 3, 1996). Such genes are generally employed where one does not wish to destroy the targeted cell, but merely to prevent the hyperproliferation of such cells. These genes are particularly useful in the treatment of benign hyperproliferative diseases such as glaucoma surgery failure, proliferative vitreoretinopathy. Other ocular diseases associated with excessive angiogenesis such as age related macular degeneration, retinopathy of prematurity, and diabetic retinopathy may also be treated with such cytostatic genes.

5) Cytokine Genes

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the alpha, beta and gamma subtypes especially interferon α-2b and fusions such as interferon α-2α-1. In particular disease states to be treated with cytokines, it is preferred that the cytokine gene is closely regulated is a dose dependent fashion. For example when using an interferon gene in a vector targeted to liver cells, it is preferred that the promoter be able to be closely regulated by an exogenous substance such as through the use of the GeneSwitch™ regulatory system (GeneMedicine, Inc. Woodlands, Tex.).

6) Chemokine Genes

The term "chemokine gene" refers to a nucleotide sequence, the expression of which in a cell produces a cytokine. The term chemokine refers to a group of structurally related low-molecular cytokines weight factors secreted by cells are structurally related having mitogenic, chemotactic or inflammatory activities. They are primarily cationic proteins of 70 to 100 amino acid residues that share four conserved cysteine residues. These proteins can be sorted into two groups based on the spacing of the two aminoterminal cysteines. In the first group, the two cysteines are separated by a single residue (C—x—C), while in the second group, they are adjacent (C—C). Examples of member of the 'C—x—C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and I (AMCF-I and -II), pre-B cell growth stimulating factor (PBSF),and IP10. Examples of members of the 'C—C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP4), macrophage inflammatory protein 1 α(MIP-1-α), macrophage inflammatory protein 1 β(MIP-1-β), macrophage inflammatory protein 1 γ(MIP-1-γ), macrophage inflammatory protein 3-α(MIP-3-α, macrophage inflammatory protein 3 β(MIP-3-β), chemokine (ELC), macrophage inflammatory protein 4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3, mouse protein C10.

7) Pharmaceutical Protein Genes

The term "pharmaceutical protein gene" refers to nucleotide sequence, the expression of which results in the production of protein have pharmaceutically effect in the target cell. Examples of such pharmaceutical genes include the proinsulin gene and analogs (as described in PCT International Patent Application No. WO98/3 1397, growth hormone gene, dopamine, serotonin, epidermal growth factor, GABA, ACTH, NGF, VEGF (to increase blood perfusion to target tissue, induce angiogenesis, PCT publication WO98/328959 published Jul. 30, 1998), thrombospondin, etc.

8) Proapoptotic Genes

The term "pro-apoptotic gene" refers to a nucleotide sequence, the expression thereof results in the programmed cell death of the cell. Such genes are particularly useful in the destruction of the targeted cell for use in cancer therapy. Examples of pro-apoptotic genes include p53, adenovirus E3-11.6K, the adenovirus E4 or f4 gene, p53 pathway genes, and genes encoding the caspases.

9) Pro-Drug Activating Genes

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine (5-FC) to 5-fluorouracil (5-FU), a potent antitumor agent. The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir can be employed.

10) Anti-Angiogenic and Angiogenesis-Inducing Genes

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in *Proc. Nat'l. Acad. Sci. USA* (1998) 95:8795–8800), endostatin.

Also of interest are angiogenesis-inducing genes that encode, for example, vascular endothelial growth factor, and other polypeptides that induce angiogenesis. Such genes are useful for treating ischemia and other vascular disorders.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the delta13–19 amino acids to eliminate the calpain consensus cleavage site, modifications to the oligomerization domains (as described in Bracco et al. PCT published application WO97/0492 or U.S. Pat. No. 5,573,925).

Furthermore, the above therapeutic genes can be secreted into the media or localized to particular intracellular locations by inclusion of a targeting ligand such as a signal peptide or nuclear localization signal (NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding non-infected cells to a diameter of approximately 16 cells wide. This system is particularly useful in conjunction with transcriptionally active proteins (e.g. p53) as the fusion proteins are efficiently transported to the nuclei of the surrounding cells. See, e.g., Elliott, G. & O'Hare, P. (1997) *Cell* 88:223–233; Marshall, A. & Castellino, A. (1997) *Nature Biotechnology* 15:205; O'Hare et al. PCT publication WO97/05265 published Feb. 13, 1997. A similar NLS derived from the HIV Tat protein is also described in Vives et al. (1997) *J. Biol. Chem.* 272:16010–16017.

Additionally, it will be readily apparent to those of skill in the art that a viral or other vector can be engineered to encode more than one therapeutic transgene. The transgenes can be the same (for example to increase the effective gene dosage) or different to achieve complementary effects. Each transgene can be under control of the same promoter (for example through the use of IRES elements) or different promoters. In those situations where it is desirable to produce a vector containing multiple transgenes, it is preferred to use minimal vector systems. The construction of such minimal vectors (also termed "gutted" or "gutless" vectors) are described in Zhang, et al. International Publication No WO9854345A1 and Morsy and Caskey (1999) *Molecular Medicine Today*, January 1999 issue, pp.18–24.

2. Other Therapeutic Agents

The terms "therapeutic agent", "therapeutic composition", and "therapeutic substance" refer, without limitation, to any composition that can be used to the benefit of a mammalian species. Such agents may take the form of ions, small organic molecules, peptides, proteins or polypeptides, oligonucleotides, and oligosaccharides, for example.

B. Diagnostic Applications

The complexes of the invention also find use in diagnostic and labeling applications. A coordinate covalent linkage mediated by a metal ion joins a targeting moiety to a detectable label. The label can be present on a viral or other vector, on a liposome, or can be attached to a molecule that includes a label. Upon administration to an organism, or to a population of cells, the targeting moiety will mediate attachment of the label to the targeted cells or tissues. One can then detect the presence of the label to determine which cells and/or tissues have the moiety to which the targeting ligand is directed. Also, as previously discussed, a heavy metal visualizable through conventional diagnostic procedures can be employed, providing the ability to follow the targeted therapeutic complex through the organism non-invasively and thus providing both therapeutic and diagnostic value.

Detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, NY and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green", rhodamine and derivatives (e.g., Texas red, tetrarhodimine isothiocynate (TRITC), etc.), digoxigenin, biotin, phycoerythrin, AMCA, CyDyes", and the like), radiolabels (e.g., 3H, 125I, 35S, 14C, 32P, 33P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase or luciferase) with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to targeting ligands using the coordinate covalent linkages of the invention include, e.g., luciferase, and horse radish peroxidase. The chemiluminescent substrate for luciferase is luciferin. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl)spiro[1,2-dioxetane-3, 2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4ClN), which are detected visually. Other suitable substrates are known to those skilled in the art.

In general, a detector which monitors a particular label is used to detect the label. Typical detectors include spectrophotometers, phototubes and photodiodes, microscopes, x-ray, magnetic resonance imaging (MRI), scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

C. Other Uses

The targeted vectors of the invention are also useful to introduce a gene into a host for in vivo production of a protein encoded by the gene. For example, transgenic bovines and goats are used for production of proteins in milk (see, e.g., WO 93/25567). The vectors are also useful for making "knockout" animals that are useful for the study of human diseases and other purposes.

IV. Formulations and Treatment Regimes

The complexes prepared above can be formulated for administration to a mammalian organism in accordance with techniques well known in the art. The complexes can be administered in conventional solutions such as sterile saline and can incorporate one or more carriers of agents to preserve the stability and sterility of the solution. The formulations can also include carrier molecules conventionally used in the formulation of pharmaceutical agents. The term "carriers" refers to compounds commonly used on the formulation of pharmaceutical compounds used to enhance stability, sterility and deliverability of the therapeutic compound. When the viral, non-viral or protein delivery system is formulated as a solution or suspension, the delivery system is in an acceptable carrier, preferably an aqueous carrier. A variety of aqueous carriers can be used, e.g., water, buffered water, 0.8% saline, 0.3% glycine, hyaluronic acid and the like.

These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The formulations can also include delivery enhancing agents to increase uptake of the targeted complexes into the target cells. The terms "delivery enhancers" or "delivery enhancing agents" are used interchangeably herein and includes agents that facilitate the transfer of the nucleic acid or protein molecule to the target cell. Examples of such delivery enhancing agents detergents, alcohols, glycols, surfactants, bile salts, heparin antagonists, cyclooxygenase inhibitors, hypertonic salt solutions, and acetates. Suitable alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Bile salts such as taurocholate, sodium taurodeoxycholate, deoxycholate, chenodesoxycholate, glycocholic acid, glycochenodeoxycholic acid and other astringents such as silver nitrate can be used. Heparin-antagonists like quaternary amines such as protamine sulfate can also be used. Anionic, cationic, zwitterionic, and nonionic detergents can also be employed to enhance gene transfer. Exemplary detergents include but are not limited to taurocholate, deoxycholate, taurodeoxycholate, cetylpyridium, benalkonium chloride, Zwittergent 3-14 detergent, CHAPS (3-[(3-Cholamidopropyl)dimethylammoniol]-1-propanesulfonate hydrate), Big CHAP, Deoxy Big CHAP, Triton-X-100 detergent, C12E8, Octyl-B-D-Glucopyranoside, PLURONIC-F68 detergent, Tween 20 detergent, and TWEEN 80 detergent (CalBiochem Biochemicals). Particularly preferred delivery enhancing reagents are derivatives of particular impurities that are found in some preparations of Big CHAP; these derivatives are described in PCT Application No. US98/14241 (published Jan. 21, 1999 as WO99/02191).

The formulations of the invention are typically administered to enhance transfer of an agent to a cell. The cell can be provided as part of a tissue, such as an epithelial membrane, or as an isolated cell, such as in tissue culture. The cell can be provided in vivo, ex vivo, or in vitro. The formulations containing delivery enhancing compounds and modulating agents can be introduced into the tissue of interest in vivo or ex vivo by a variety of methods. In some embodiments of the invention, the modulating agent is introduced to cells by such methods as microinjection, calcium phosphate precipitation, liposome fusion, or biolistics. In further embodiments, the therapeutic agent is taken up directly by the tissue of interest.

In some embodiments of the invention, the targeted complexes of the invention are administered ex vivo to cells or tissues explanted from a patient, then returned to the patient. Examples of ex vivo administration of therapeutic gene constructs include Arteaga et al., *Cancer Research* 56(5):1098–1103 (1996); Nolta et al. *Proc. Nat'l Acad. Sci. USA* 93(6):2414–9 (1996); Koc et al., *Seminars in Oncology* 23 (1):46–65 (1996); Raper et al., *Annals of Surgery* 223(2): 116–26 (1996); Dalesandro et al., *J. Thorac. Cardi. Surg.*, 11(2):416–22 (1996); and Makarov et al., *Proc. Nat'l. Acad. Sci. USA* 93(1):402–6 (1996).

It will be appreciated by those of skill in the art that the particular dosage of a given complex will depend on a variety of factors. The targeted complexes of the present invention provide an advantage over their non-targeted counterparts in that a lower dosage can achieve an equivalent therapeutic or diagnostic effect. However, this does not necessarily mean that a reduced dosage will be indicated in all cases. For example, in oncology applications, administration of the maximum tolerated dose of the therapeutic agent is generally accepted as the preferred dosage. Clinical trials in human beings have indicated that a dose of $2.5 \times 10^{13}$ adenoviral particles administered for 5 consecutive days for three courses of therapy is well tolerated (Nielsen et al. (1998) *Hum Gene Ther.* 9: 681–94). Consequently, viral doses of this magnitude would be suitable for therapeutic applications. For oncology applications the therapeutic agent may also be combined with other treatment regimens such as radiation, etc.

In non-oncology therapeutic applications and diagnostic applications, a more limited dose would be preferred. Again, the precise nature of the dose will depend on the type of delivery vehicle, the therapeutic or diagnostic effect sought, the degree of control of transgene, expression in addition to more common factors such as the patient's age, weight, sex, physical condition, etc. However, the determination of appropriate dose is a matter of routine experimentation to those of skill in the art. Dose escalation trials in mammalian species generally are initially carried out in small animal species such as swine, eventually in primates. Phase I clinical trials in human beings also include such dose escalation and toxicity assessments. Although such experiments are time-consuming, the skill necessary to achieve the clinically relevant dosage range is a matter of routine experimentation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

I claim:

1. A targeted complex of the formula:

{{recombinant virus-CM}-TMI-{CM-targeting ligand}};

wherein CM is a chelating peptide, TMI is a transition metal ion, and CM-targeting ligand is a chelating peptide (CM) covalently linked to a targeting ligand.

2. The complex of claim 1, wherein the virus lacks a native viral ligand that binds to a native cellular receptor for the virus.

3. The complex of claim 1, wherein the virus is replication competent.

4. A The complex of claim 1, wherein the virus is replication deficient.

5. The complex of claim 1, wherein the virus includes a polynucleotide that encodes and expresses a p53 tumor suppressor polypeptide and the targeting ligand is an antibody that binds to a tumor antigen.

6. The complex of claim 1, wherein the virus is an adenovirus.

7. The complex of claim 6, wherein the adenovirus comprises a viral coat protein and the viral coat protein is selected from the group consisting of a fiber, a penton and a hexon.

8. The complex of claim 6, wherein the adenovirus comprises a tissue-specific or a tumor-specific promoter to drive of an early viral gene and selectively replicates in a specific tumor or tissue type.

9. The complex of claim 8, wherein the adenovirus is a wild-type adenovirus.

10. The complex of claim 6, wherein the adenovirus is replication deficient.

11. The complex of claim 10, wherein the genome of the adenovirus comprises a partial or total of the adenovira E1 region.

12. The complex of claim 10, wherein the genome of the adenovirus comprises a partial or total deletion of the protein IX-encoding region.

13. The complex of claim 1, wherein the virus is selected from the group consisting of a retrovirus, a vaccinia virus, a herpes virus, an adeno-associated virus, a minute virus of mice (MVM), a human immunodeficiency virus, a sindbis virus, an MoMLV, and a hepatitis virus.

14. The complex of claim 1, wherein the targeting ligand is an antibody.

15. The complex of claim 14, wherein the antibody is reactive with a tumor antigen.

16. The complex of claim 14, wherein the antibody is selected from the group consisting of Fab, Fab', $Fab_2$' and Fv fragments.

17. The complex of claim 14, wherein the antibody is a human antibody.

18. The complex of claim 14, wherein the antibody is a single chain antibody.

19. The complex of claim 18, wherein the single chain antibody is reactive with carcinoembryonic antigen.

20. The complex of claim 1, wherein the targeting ligand comprises a conformationally constrained peptide.

21. The complex of claim 20, wherein the conformationally constrained peptide comprises a portion of an adenoviral fiber protein.

22. The complex of claim 1, wherein the recombinant virus is a paramyxovirus.

23. A viral vector complex that comprises a targeting ligand that is attached to a surface polypeptide of a viral vector by a coordinate covalent linkage mediated by a transition metal ion.

24. A method of producing a kinetically inert targeted recombinant virus complex, the method comprising:

a) preparing a kinetically labile transition metal complex by contacting recombinant virus-CM and a CM-targeting ligand with a transition metal ion that is in a kinetically labile oxidation state; and b) changing the oxidation state of the metal ion to form the kinetically inert complex.

25. The method of claim 24, wherein the kinetically labile transition metal complex is prepared by:

a) contacting the CM-targeting ligand with the transition metal ion in a reaction vessel and allowing the transition metal ion to bind to the CM to form a transition metal ion-CM-targeting ligand complex;

b) removing uncomplexed transition metal ion from the reaction vessel; and c) contacting the transition metal ion-CM-targeting ligand complex with the recombinant virus-CM and allowing the transition metal ion to bind to the CM to form the complex.

26. The method of claim 24, wherein the kinetically labile transition metal complex is prepared by contacting the CM-targeting ligand and the recombinant virus-CM with the transition metal ion simultaneously.

* * * * *